(12) United States Patent
Pant et al.

(10) Patent No.: US 6,461,314 B1
(45) Date of Patent: Oct. 8, 2002

(54) INTRABODY HIFU APPLICATOR

(75) Inventors: Bharat B. Pant, Sony Brook; David E. Acker, Setauket, both of NY (US); Edward Paul Harhen, Duxbury, MA (US)

(73) Assignee: Transurgical, Inc., Setauket, NY (US)

( * ) Notice: Subject to any disclaimer, the term of this patent is extended or adjusted under 35 U.S.C. 154(b) by 0 days.

(21) Appl. No.: 09/496,988

(22) Filed: Feb. 2, 2000

Related U.S. Application Data

(60) Provisional application No. 60/118,432, filed on Feb. 2, 1999.

(51) Int. Cl.[7] ............................. A61H 1/00; A61H 1/02; A61H 5/00
(52) U.S. Cl. ............................. 601/2; 600/439; 604/22
(58) Field of Search .......................... 601/2; 600/437, 600/439; 606/27; 607/88, 92, 96, 97; 604/22

(56) References Cited

U.S. PATENT DOCUMENTS 5,135,001 A    8/1992   Sinofsky et al. ....... 128/662.06
5,471,988 A  * 12/1995  Fujio et al. ........... 128/660.03

FOREIGN PATENT DOCUMENTS

JP    359114994 A    7/1984

OTHER PUBLICATIONS

Kojima, T. Matrix Array Transducer and Flexible Matrix Array Transducer, Nihon Dempa Kogyo Co. Ltd., 1986 IEEE, Ultrasonics Symposium, pp. 649–654.

* cited by examiner

*Primary Examiner*—Marvin M. Lateef
*Assistant Examiner*—Jeoyuh Lin
(74) *Attorney, Agent, or Firm*—Lerner, David, Littenberg, Krumholz & Mentlik, LLP

(57) ABSTRACT

An apparatus and method for applying sonic energy within the body of the living subject. A probe for applying sonic energy within the body of a subject includes a probe body having a proximal and a distal end adapted for insertion into the body of a subject, a spatially-distributed sonic transducer disposed adjacent to the distal end of the probe body and a device for moving one portion of the spatially-distributed transducer relative to another portion of the transducer while the distal end of the probe is disposed within the body of the subject.

19 Claims, 10 Drawing Sheets

INTRABODY HIFU APPLICATOR

CROSS REFERENCE TO RELATED APPLICATIONS

This application claims the benefit of provisional patent application Ser. No. 60/118,432 filed on Feb. 2, 1999, the disclosure of which is incorporated by reference herein.

FIELD OF THE INVENTION

The present invention relates to application of sonic energy, such as focused ultra sound energy within the body of a living subject such a human or other mammalian subject.

BACKGROUND OF THE INVENTION

Various forms of therapy can be applied within the body of a human or other mammalian subject by applying energy from outside of the subject. In hyperthermia, ultrasonic or radio frequency energy is applied from outside of the subject's body to heat the tissues. The applied energy can be focused to a small spot within the body so as to heat the tissues at such spot to a temperature sufficient to create a desired therapeutic effect. This technique can be used to selectively destroy unwanted tissue within the body. For example, tumors or other unwanted tissues can be destroyed by applying heat to heat the tissue to a temperature sufficient to kill the tissue, commonly to about 60° to 80° C., without destroying adjacent normal tissues. Such a process is commonly referred to as "thermal ablation". Other hyperthermia treatments include selectively heating tissues so as to selectively activate a drug or promote some other physiologic change in a selected portion of the subject's body. Other therapies use the applied energy to destroy foreign objects or deposits within the body as, for example, in ultrasonic lithotripsy.

In most cases, the focused ultrasound energy used in said procedures is applied by an ultrasonic energy source disposed outside of the body. For example, certain embodiments taught in co-pending, commonly assigned U.S. patent application Ser. No. 09/083,414 files May 22, 1998 and in the corresponding International Application PCT/US98/10623, also filed May 22, 1998, the disclosures of which are hereby incorporated by reference herein, describe systems for applying focused ultrasound energy in conjunction with a magnetic resonance device. An external ultrasonic energy applicator is also taught for example, in FIG. 1 of Aida et al., U.S. Pat. No. 5,590,653 and in FIG. 1 of Oppelt et al., U.S. Pat. No. 5,624,382. These external ultrasonic energy sources transmit ultrasonic energy to the desired treatment location through the tissues of the body. Various proposals have been advanced for inserting ultrasonic energy sources into the body and focusing energy from such intrabody sources on the desired treatment regions. For example, FIG. 5 of the aforementioned Oppelt et al. '382 patent illustrates a therapeutic ultrasound transducer which may be inserted into the rectum so as to direct ultrasonic energy onto the prostate gland through the wall of the rectum. Aida et al. '653 discloses various forms of intrabody transducer arrays (FIGS. 9–12). Diederich, *Transuretheral Ultrasound Array For Prostate Thermal Therapy: Initial Studies, IEEE Transactions On Ultrasonics, Ferroelectrics and Frequency Control*, Vol. 43, No. 6, pp. 1011–1022 (November 1996) discloses a rod-like ultrasound transducer housed within a catheter. Such a rod-like transducer does not focus the ultrasound but instead provides a sound pressure distribution which is at a maximum adjacent the transducer and which diminishes with distance. In use, the transducer is inserted into the urethra and the catheter is cooled by a flow of water. The cooling water limits the temperature rise of the urethra wall. Prostate tissue remote from the urethra is heated by the applied energy.

Despite these and other attempts to utilize intrabody ultrasonic transducers, still further improvement would be desirable.

SUMMARY OF THE INVENTION

One aspect of the present invention provides a probe for applying sonic energy within the body of the subject. The probe according to this aspect of the invention includes a probe body having a proximal and having a distal end adapted for insertion into the body of the subject. The probe also includes a spatially distributed ultrasonic transducer disposed adjacent the distal end of the probe body. As used in this disclosure, the term "spatially distributed sonic transducer" refers to a sonic transducer which is capable of emitting sound from a plurality of locations spaced apart from one another. One form of a spatially distributed transducer includes a plurality of discrete transducer elements mounted at spaced apart locations. Another form of spatially distributed transducer includes a continuous sheet of transducer material. In such a continuous-sheet transducer, various regions of the sheet are spaced apart from one another and hence can emit sound at spaced apart locations. The probe according to this aspect of the invention further includes means for moving one portion of the distributed transducer relative to another portion of the distributed transducer while distal end of the probe and hence the distributed transducer is disposed within the body of the subject. Such movement changes the configuration of the distributed transducer so as to focus the sound emitted from the distributed transducer onto a focal spot at a selected location relative to the probe.

The distributed transducer may include a deformable element, which may be separate from the active elements of the transducer. Alternatively, the deformable element may be integral with a continuous transducer sheet. In the simplest embodiment, the entire distributed transducer includes only a continuous sheet element, such as an elongated strip formed from a piezoelectric material and the electrodes used to actuate those portions of the material. Alternatively, the distributed transducer may include plural separate transducer elements mounted to the deformable element at spaced-apart locations. The deformable element may incorporate an elongated beam having a fixed end mounted to the probe body and a fixed end. The means for controlling deformation may include a control element moveable mounted to the probe body. The control element desirably is a flexible cable having a distal end connected to the free end of the beam and having a proximal end extending to the proximal end of the probe body. Thus, the deformable element may be bent to the desired degree of curvature by pulling the flexible cable. Alternatively, the deformable element may include a disc like element having a central region and a peripheral region surrounding the central region. The means for controlling deformation may include means from moving the peripheral and central regions relative to one another.

In yet another alternative, the probe may include a plurality of supports movably mounted to the probe body adjacent to distal end thereof and the distributed transducer may include a plurality of transducer elements mounted to the supports. The means for moving one part of the transducer relative to the other may include means for moving one or more of the supports relative to the probe body. For example, the plurality of supports may include a plurality of elongated supports arranged generally in the manner of the radial ribs of an umbrella. Thus, the elongated supports may have central ends pivotally connected to a common member and may have peripheral ends remote from the central ends. The transducer elements are mounted to the elongated supports adjacent the peripheral ends thereof. The supports can be pivoted relative to the common member between a collapsed condition in which the peripheral ends are close to a central axis and an expanded commission in which the peripheral ends are remote from the central axis. The pivoting means may include a control member and a plurality of struts. Each strut has a first end pivotally connected to the control member and a second end connected to one of the elongated supports remote from the central end of such support. The means for pivoting the supports may include means for moving the control member and common member relative to one another. For example the probe body may include an elongated tubular element and a flexible cable may be provided in the tubular element. The cable may be attached to the control member and the distal end of the tubular element may be connected to the common member or vice versa.

In yet another arrangement, the distal end of the probe body itself may be deformable and the distributed transducer may be arranged along the distal end of the probe body so that deformation of the probe body distal end will move one part of the transducer relative to another part. For example, the probe body may be elongated and the distributed transducer may include separate transducers or portions of a continuous sheet spaced apart from one another in the lengthwise direction along the probe body. The means for deforming the distal end of the probe body may include means for bending the distal end of the probe body transverse to its lengthwise direction so as to vary the curvature of the distributed transducer. The distal end of the probe body may be advanced into an intrabody space and the probe body may be deformed while the distal end is disposed in the intrabody space. For example, the probe body may be advanced through the urethra into the urinary bladder and the distal end of the probe body may be bent while the distal end of the probe body is in the urinary bladder.

A further aspect of the present invention provides probe for applying sonic energy within the body of the subject which includes an elongated probe body having a distal end and a spatially distributed sonic transducer disposed adjacent to the distal end of the probe body. In a probe according to this aspect of the present invention, the distributed transducer is moveable between a collapsed condition in which the distributed transducer has relatively small dimensions in directions transverse to the direction of elongation of the probe body and an expanded condition in which the distributed transducer has relatively large transverse dimensions and hence extends outwardly from the probe body in one or more directions transverse to the direction of elongation of the probe body. A probe according to this aspect of the invention desirably includes means for controlling movement of the distributed transducer between the collapsed condition and the expanded condition. In a probe according to this aspect of the invention, the movement control means optionally may be adapted to vary the configuration of the distributed transducer while the transducer is in the expanded condition so as to vary the focus of sound waves emitted by the transducer.

Still further aspects of the present invention provide methods of ultrasonic treatment.

DETAILED DESCRIPTION OF THE PREFERRED EMBODIMENTS

Figure 2:
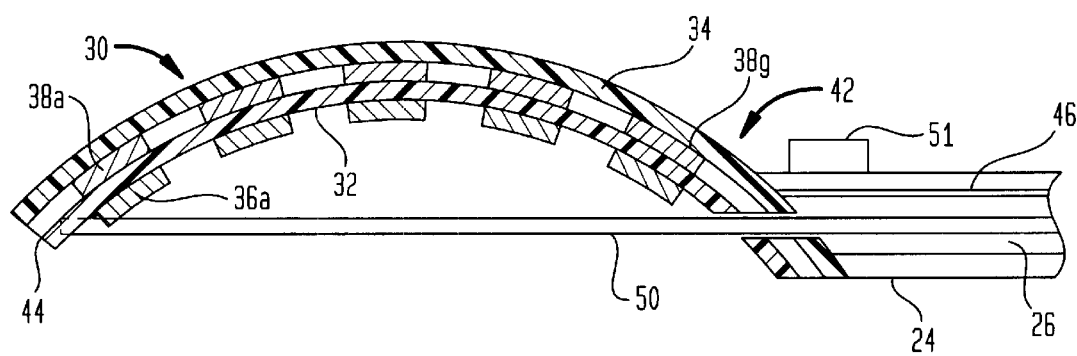
FIG. 2 is a fragmentary, diagrammatic sectional view depicting a portion of the probe of FIG. 1.
Figure 3:
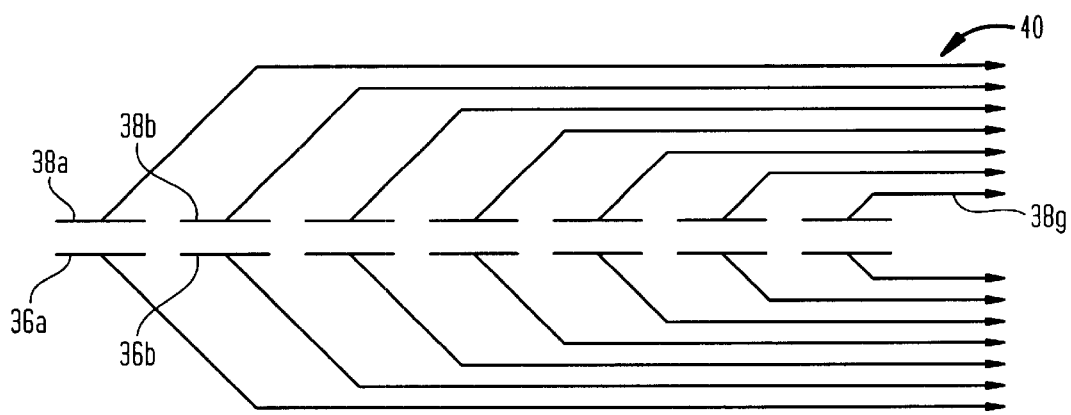
FIG. 3 is a fragmentary electrical schematic of the probe of FIGS. 1–2.

A probe in accordance with one embodiment of the present invention includes a probe body 20 having a proximal end 22 and a distal end 24 adapted for insertion into the body of a subject. Probe body 20 may be a conventional catheter, endoscope or other conventional medical device. The particular probe body illustrated is in the form of an elongated tube having an interior bore 26 extending between the proximal and distal ends. A deformable distributed sonic transducer 30 is mounted to the distal end 24 of the probe body. As best seen in FIG. 2, transducer 30 includes a continuous sheet 32 of a piezoelectric polymeric material such as a polyvinyledene fluoride piezoelectric material. Materials of this type are described in U.S. Pat. Nos. 4,830,795, 4,268,653 and 4,577,132. Particularly preferred piezoelectric polymers are available from Measurement Specialties, Inc. of Norristown, Pennsylvania. The transducer further includes a backing layer 34 and electrodes 36 and 38 disposed on opposite sides of piezoelectric layer 32. Layer 34 may be formed, for example, from a flexible dielectric polymer, a flexible metal strip, or the like. The electrodes are formed in pairs. Each pair includes a first electrode 36 disposed on one side of the piezoelectric layer 32 and a second electrode 38 disposed on the opposite side of the piezoelectric layer, in alignment with the first electrode. For example, electrodes 36a and 38a (FIGS. 2 and 3) form one such pair whereas electrodes 36b and 38b (FIG. 3) form another such pair. The electrodes are connected to conductors 40 extending along layers 32 and 34. These conductors may be fabricated, for example, by techniques such as those used in formation of flexible printed circuits.

The thicknesses of the various elements are greatly exaggerated for clarity of illustration in FIG. 2. In practice, the entire transducer is formed as an integral, strip-like structure. Thus, the electrodes may be provided as thin, electrically-conductive coatings on opposite sides of layer 32.

Transducer 30 is generally in the shape of an elongated, flexible beam having a fixed end 42 attached to the distal end 24 of probe body 20 and having a free end 44 remote from the fixed end. The electrode pairs 36, 38 are arranged along the lengthwise extent of the beam. Conductors 40 are connected to further conductors 46, which a few are seen in FIG. 2. Conductors 46 extend to the proximal end 22 of the probe body, and to an electrical connector 48 (FIG. 1) at the proximal end of the probe body.

A control element in the form of a flexible cable 50 is attached to the free end 44 of the beam or transducer 30. Cable 50 is slideably received within the bore 26 of the probe body and extends to a proximal end element 52. End element 52 in turn is connected through a linkage 54 to the proximal end 22 of the probe body. Linkage 54 includes a mechanical device for controlling the position of proximal end element 52 relative to the proximal end of the probe body, and hence controlling the position of the control element 50 relative to probe body 20. The particular linkage illustrated includes a manually adjustable wheel 56, a threaded rod 58 and a nut 60 threadedly engaged on rod 58. Wheel 56 and screw 58 are rotatably mounted to one element of the linkage, whereas nut 60 is pivotally mounted to another element of the linkage, so that by rotating knob 56 and screw 58, the linkage can be expanded or collapsed, thereby driving proximal end element 52 forwardly and rearwardly relative to the probe body. The particular linkage depicted in FIG. 2 is merely exemplary. Any other conventional positioning device capable of moving one element to a desired position relative to the other can be employed. For example, cams, levers, electromechanical actuators and hydraulic actuators may be employed. Also, the linkage may be omitted, so that the proximal end element 52 can be moved manually relative to the proximal end of the probe body. The probe may also be provided with a separate device (not shown) for selectively locking the control element or cable 50 in position relative to the probe body.

Figure 1:
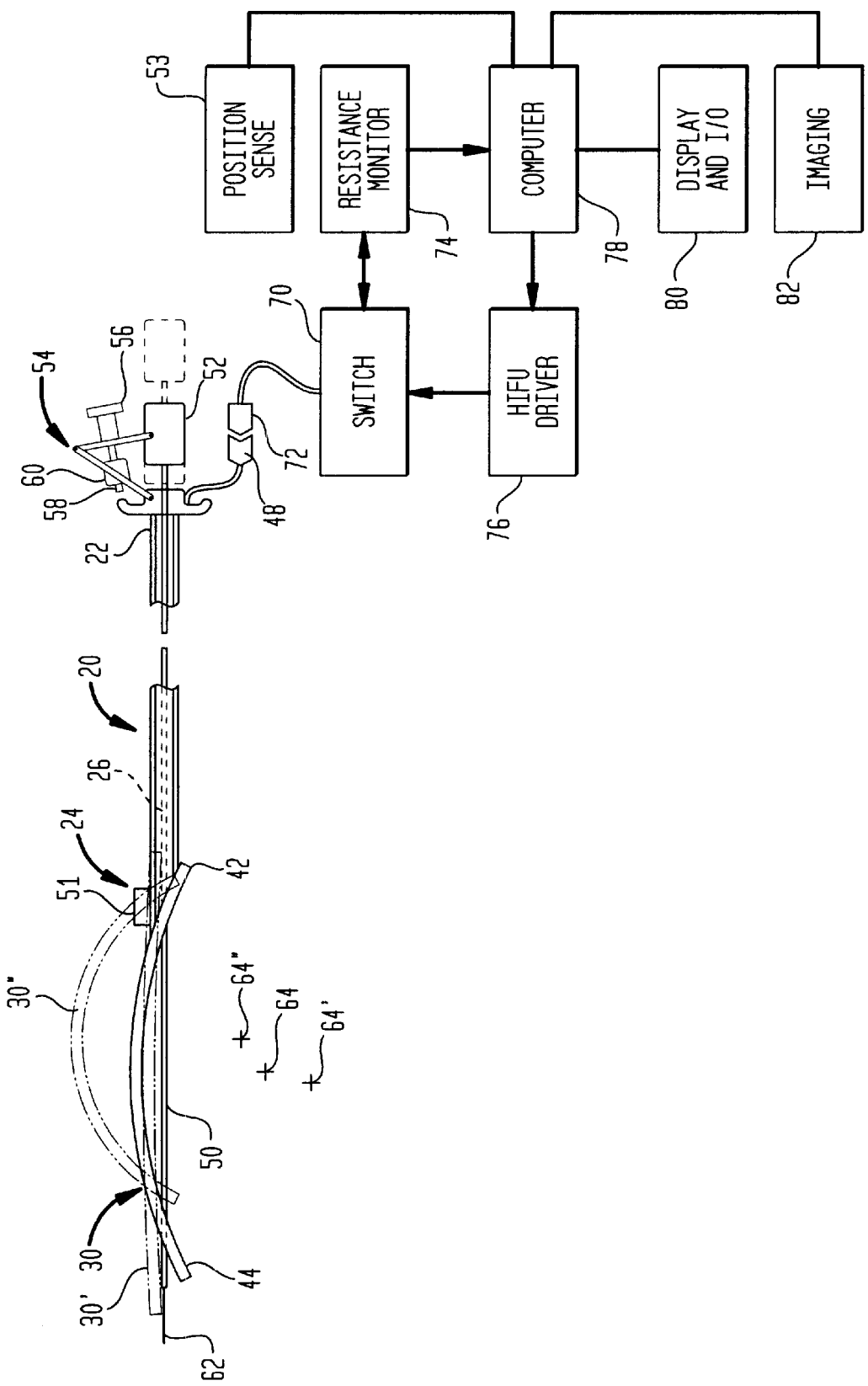
FIG. 1 is a diagrammatic view depicting a probe in accordance with one embodiment of the invention in conjunction with other apparatus.

Beam or transducer 30, in its free undeformed condition is nearly flat, as indicated in broken lines at 30' in FIG. 1. By moving control element or cable 50 in the retracting direction, toward the proximal end 22 of the probe body, the free end 44 of the beam can be brought closer to the fixed end 42, thereby deforming the transducer or beam into configurations having a greater curvature, including the fully bowed condition illustrated in broken lines in FIG. 1 at 30" and also illustrated in FIG. 5. In the fully elongated or collapsed condition 30', the beam lies close to the axis 62 of the probe body distal end. In the fully bowed or expanded condition 30", the probe projects laterally from axis 62.

Figure 4:
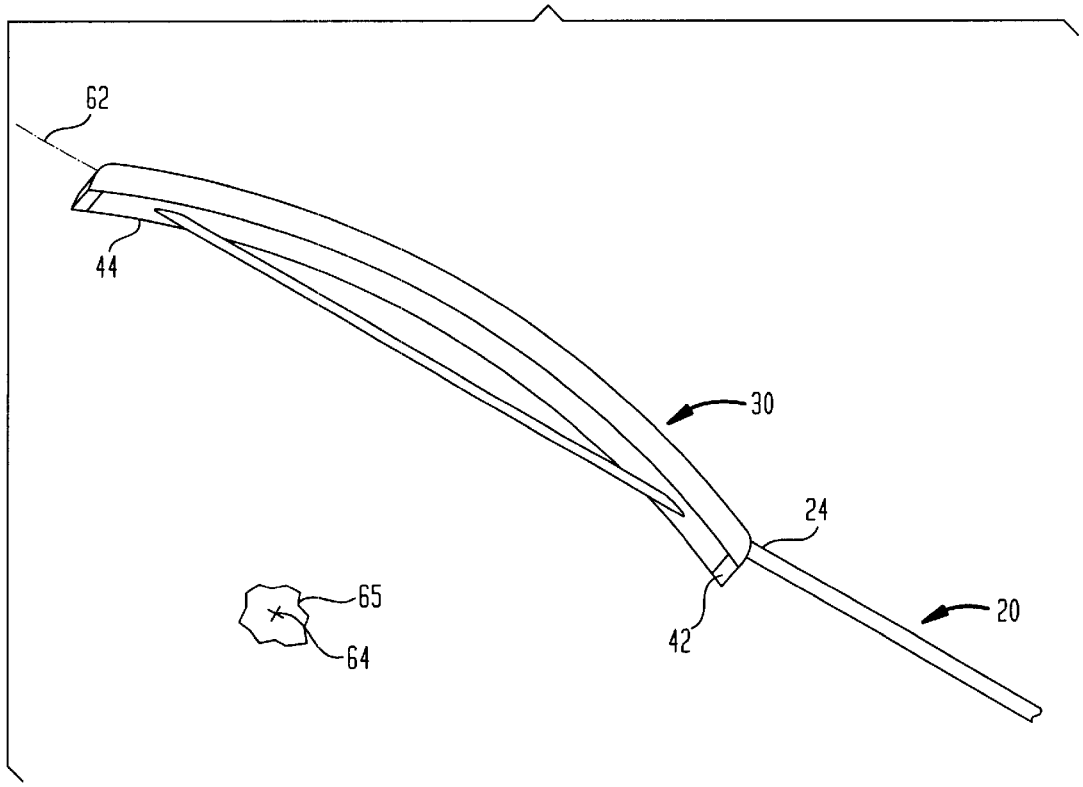
FIG. 4 is a fragmentary, perspective view depicting the probe of FIGS. 1—3 in one condition.
Figure 5:
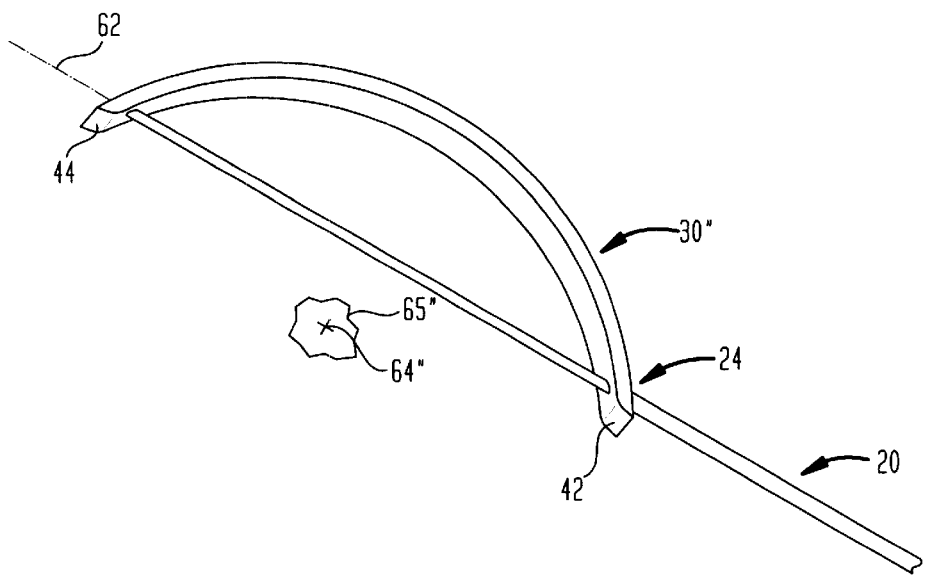
FIG. 5 is a view similar to FIG. 4 but depicting the probe in a different condition.

As further discussed below, the transducer can be actuated as a multielement array to provide ultrasonic emissions focused on a focal within a focal region 65 near the center of curvature 64 of the beam. The focal spot can be moved within the focal region by altering the phasing of the electrical signal supplied to the array. However, bending the transducer moves the center of curvature and moves the focal region. With the transducer in the fully collapsed or flat condition, the focal spot will lie at a large distance from axis 62. As the transducer becomes progressively more bowed, the center of curvature 64 and hence the focal region and focal spot move closer to axis 62. With the transducer in the slightly bowed position illustrated in solid lines in FIG. 1 and illustrated in FIG. 4, the center of curvature 64 is at the position indicated. With the transducer in a more bowed position, as indicated in broken lines at 30" in FIG. 1 and as shown in FIG. 5, the center of curvature is at position 64".

The probe is used in conjunction with monitoring and driving elements (FIG. 1). A switch 70 is connected by a multiconductor cable to a connector 72 matable with connector 48. An impedance measuring device 74 is provided. The impedance measuring device can be connected by switch 70 to a pair of electrodes 38a and 38g disposed at opposite ends of transducer 30, so that the impedance measuring device can measure the electrical impedance within piezoelectric layer 32, from one end of the piezoelectric layer to the other. Thus, electrodes 38a and 38g serve as impedance measuring electrodes. The impedance monitoring device may include a conventional bridge circuit, with the impedance between electrodes 38a and 38g on one leg of the bridge circuit. The impedance monitor may also include temperature compensation elements (not shown) mounted at the distal end of the probe and connected in the bridge circuit so as to compensate for effects of temperature on the impedance on layer 32. The impedance monitor may also include conventional components such as operational amplifiers and analog-to-digital converters for providing a digital readout of the impedance between electrodes 38a and 38g. Desirably, the impedance monitoring device is arranged to monitor AC impedance rather than DC resistance.

The electrical impedance within piezoelectric layer 32 varies with mechanical strain on the layer. As the beam is bent from undeformed, fully collapsed condition 30' toward the fully expanded bowed condition 30", layer 32 is placed under progressively increasing compression and the electrical impedance within the layer. Thus, the electrical impedance between electrodes 38a and 38g through layer 32 varies with the degree of curvature in the beam.

During operation of the impedance monitoring device, electrodes 36 and 38 which are not connected to the resistance monitoring device are inactive. Depending on the configuration and placement of the electrodes, a significant portion of the impedance along the piezoelectric layer may be shorted by conductivity along the inactive electrodes. To avoid such shorting, and increase the change in resistance between electrodes 38a and 38g, the intermediate electrodes 38b, 38c . . . and 36b, 36c . . . may be isolated from the piezoelectric layer by a very thin dielectric layer (not shown) disposed between the electrodes and the surface of the piezoelectric layer. Switch 70 is also arranged to disconnect electrodes 38a and 38g from resistance monitor 74 and to connect all of the electrodes 36 and 38 to a HIFU driver 76. HIFU driver 76 includes conventional phased array driver components for applying electrical potentials between the electrodes 36 and 38 of each electrode pair. These electrical potentials vary at ultrasonic frequencies. The varying potential is applied across the region of piezoelectric film 32 between each pair of electrodes and causes mechanical vibration of each such region.

HIFU driver 76 is controlled by a computer 78. The computer controls the frequency and phase of the excitations applied to the various electrode pairs in accordance with the known principles governing operation of phased array ultrasonic emitters so that the ultrasonic emissions from the various parts of the piezoelectric layer reinforce one another at the desired focal spot. Computer 78 stores a value of the curvature of the transducer or beam 30 based upon the resistance measurement from resistance monitor 74. This value is incorporated into the parameters defining the geometry of the emitter array, and such parameters are used in the normal manner to calculate the appropriate signals to be applied to each element of the array. As such calculations are well within the skill of the art and employ known methods, they are not described in detail herein.

Computer 78 is linked to conventional display and input/output devices 80 such as a CRT or other pictorial display and a mouse, joystick or other control elements. An imaging system 82 such as a magnetic resonance imaging, x-ray or CAT scan imaging system 82 is also connected to the computer. The imaging system is arranged to provide data in substantially real time constituting an image of the internal structures within the patient's body in the vicinity of probe distal end 24. This representation includes a depiction of the probe distal end and the transducer 30.

A sensor 51 such as a sensor for detecting magnetic field components is also mounted to the distal end of a probe. Sensor 51 is connected by additional conductors (not shown) extending through the probe body to the proximal end thereof to a position sensing unit 53. Position sensing unit 53 may be arranged to detect the position and/or orientation of sensor 51 based upon magnetic or electromagnetic fields transmitted to or from sensor 51. As described for example, in international patent publication WO 95/09562, the disclosure of which is incorporated by reference herein, sensor 51 may be arranged to receive or transmit magnetic field components, and may be used in conjunction with additional sensors (not shown) mounted in a fixed frame of reference or in a frame of reference fixed to the appropriate portion of the patient's body. As described in these publications, position sensing unit 53 is arranged to determine the position and/or orientation of the probe distal end in such frame of reference. As also described in these patents and publications, computer 78 can combine the position and orientation of the probe distal end with the imaging data from imaging system 82 so that the position and orientation data and the imaging data are in a common frame of reference. Display 82 can display a representation of the probe distal end and transducer in the correct position relative to the displayed anatomical structures. Such a representation may be displayed in multiple views.

In operation, the probe distal end is advanced into the patient until the probe distal end is disposed adjacent the region of the patient to be treated. The probe may be advanced into naturally occurring body cavities as, for example, the gastrointestinal tract circulatory system, respiratory tract or urinary tract. While the probe is being advanced, the transducer 30 desirably is in its fully collapsed or flat position 30' (FIG. 1) so that the extent of the transducer in the directions transverse to the axis 62 of the probe distal end is small. This facilitates advancement of the probe through confined spaces within the patient's body.

Once the probe distal end is near the anatomical structure to be treated, the physician adjusts the curvature of the transducer by operating knob 56 and linkage 54 so as to move the control element or cable 50 and thereby pull the free end 44 of the transducer towards the fixed end 42 and the distal end of the probe. As the linkage is adjusted, switch 70 and resistance monitor 74 detect the curvature of the transducer. Computer 78 displays a mark on the display unit 80 at a location corresponding to the location of the center of curvature 64 of the transducer. This location and orientation is computed from the location of the probe distal end, as detected by transducer 51 and the curvature of the transducer, as measured by resistance monitor 74.

As the physician adjusts linkage 60, resistance monitor 74 registers the changed curvature of transducer 30. The computer displays the new location of center of curvature 64 superposed on the depiction of anatomical structures derived from imaging unit 82. The computer may also display a representation of focal region 65 superposed on the anatomical features. When the physician is satisfied that the center of curvature is in the appropriate location relative to the anatomical features to be treated, he then actuates the computer and HIFU driver to apply focused ultrasonic energy at one or more desired locations within the focal region 65. The design of ultrasonic phased arrays, and computer simulations of such arrays are disclosed in Ebbini, et al., Optimization of the Intensity Gain of Multiple-Focused Phased Array Heating Patterns, Int. J. Hyperthermia, 1991, Vol. 7, #6, pp. 953–973; Ebbini et al., Multiple-Focused Ultrasound Phased-Array Pattern Synthesis: Optimal Driving Signal Distributions for Hyperthermia, IEEE Transactions on Ultrasonics, Ferro Electrics and Frequency Control, Vol. 36, pp. 540–548 (1989) and Fan et al., Control Over the Necrosed Tissue Volume During Non-Invasive Ultrasound Surgery Using a 16-Element Phased Array, Medical Physics, Vol. 22 (#3), pp. 297–305 (1995). The disclosures of these articles are hereby incorporated by reference herein. The curvature of the transducer can be adjusted after application of some ultrasonic treatments so as to move the center of curvature and the beam steering region. Also, the probe may be repositioned as desired so as to shift the center of curvature and beam steering region relative to the patient.

Figure 6:
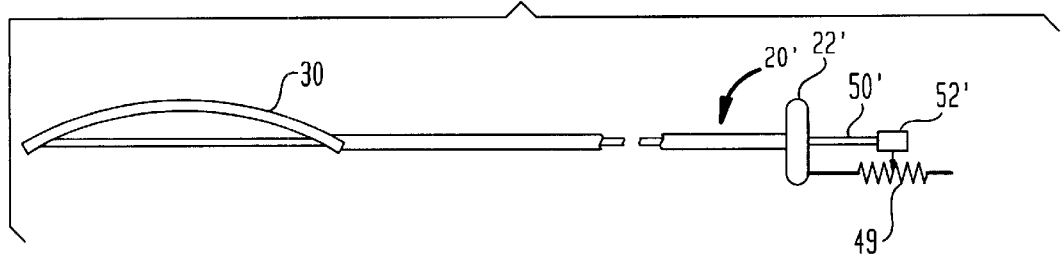
FIGS. 6, 7 and 8 are diagrammatic views of probe in accordance with further embodiments of the invention.
Figure 7:
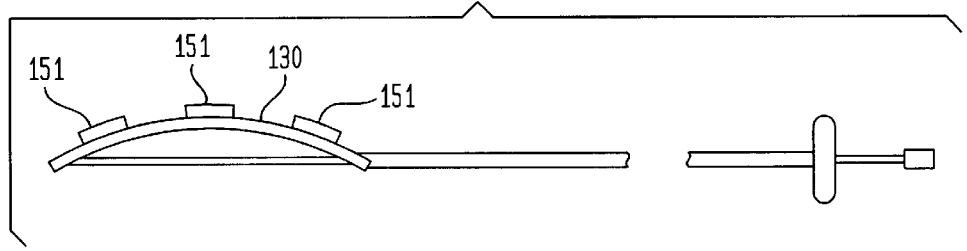

In a variant of the system discussed above, the curvature of the transducer is monitored by monitoring the position of the control element or cable 50' relative to the probe body 20". For example, a potentiometer 49 (FIG. 6), an optical encoder or other conventional position monitoring devices may be connected between the proximal end element 52' on the control cable and the proximal end 22' of the probe body. Measurements of the relative position of the control cable or control element 50' relative to the probe body 20' can be translated directly into curvature of transducer 30. In a further variant, two or more position sensors 151 (FIG. 7), similar to the position sensor 51 discussed above with reference to FIGS. 1 and 2 may be provided on the deformable transducer itself. The location and orientation of these sensors can be translated into curvature of the transducer, as well as the position and orientation of the transducer in the patient's frame of reference.

Figure 8:
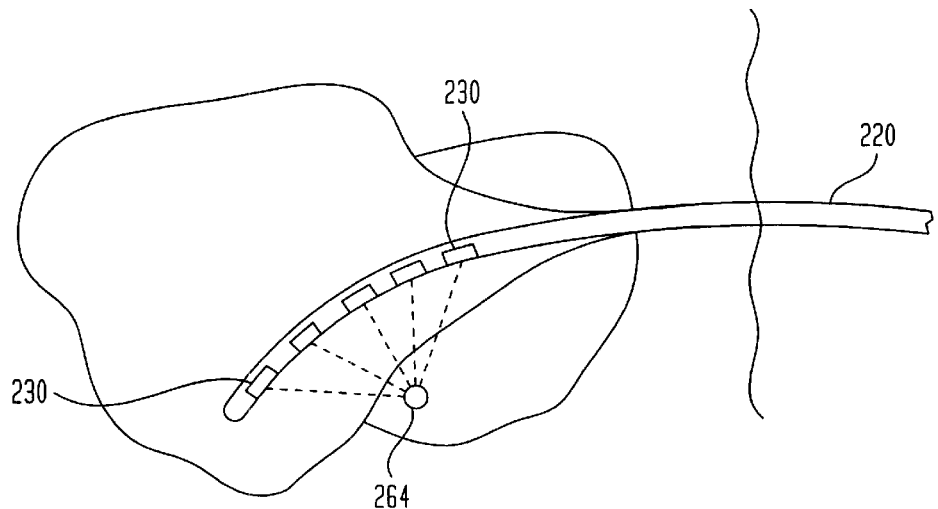

In a probe according to a further variant (FIG. 8), the transducer is provided as a set of transducer elements 230 disposed along the length of the probe body 220 itself adjacent the distal end thereof. At least the distal region of the probe body having the transducers 230 thereon is arranged for flex in a controlled fashion. The probe body may be provided with conventional devices (not shown) for bending the probe body in a controlled fashion. Transducer elements 230 may be individual, discrete transducers or else may be regions of a unitary piezoelectric sheet as discussed above with reference to FIG. 2. The transducer elements or sheet constitute a spatially-distributed transducer extending along the catheter tip. Bending of the probe body curves the array of transducer elements so that energy from the transducer elements can be focused onto a focal region 264. A flexible transducer of this type may be provided with elements such as position sensors disposed along the length of the probe or devices for detecting the degree of curvature of the probe directly. In a further variant, flexible distributed transducers as discussed above can be provided with strain gauges formed separately from the piezoelectric elements. For example, a flexible beam-like transducer may include a strain-sensitive layer forming part or all of backing layer 34, with appropriate electrodes connected to such layer. Also, a discrete strain gauge such as a strain-sensitive wire may be adhered to the beam element or embedded therein. Such strain gauges can be used to monitor the curvature of the beam or other distributed transducer.

Alternatively or additionally, curvature of the probe can be monitored by imaging the probe and detecting the curvature based upon such imaging. Detection can be accomplished visually, as by a human operator observing the displayed image of the probe and measuring the curvature on the display. Curvature also can be detected by using conventional pattern-recognition programs to detect the curved line of the probe in the data representing the image, with or without display of the image in a human perceptible form. These techniques can also be used to monitor the curvature of a separate flexible transducer such as the transducer 30 discussed above.

In further variants, individual, discrete transducer elements, rather than a single continuous piezoelectric layer, may be mounted on a flexible beam as illustrated in FIG. 2 to form a spatially-distributed transducer. In yet another variant, a spatially-distributed transducer having a continuous piezoelectric layer as discussed above with reference to FIG. 2 may be provided with only two thin, flexible electrodes, one electrode being disposed on each surface. Such a distributed transducer would not be capable of acting as a phased array. However, ultrasonic energy emitted from such a transducer can be focused by changing the curvature of the transducer.

Figure 9:
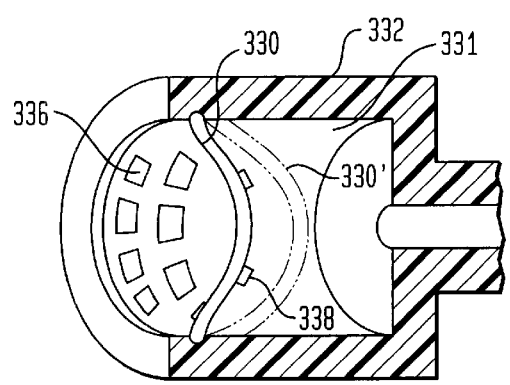
FIG. 9 is a fragmentary, diagrammatic sectional view depicting a probe in accordance with yet another embodiment of the invention.

Apparatus according to a further embodiment of the invention (FIG. 9) has a flexible transducer array 330 in the form of a diaphragm. The diaphragm is mounted in a housing 332 so that a chamber 331 defined by the housing is closed by the diaphragm. By increasing or decreasing the pressure within chamber 331, diaphragm 330 can be adjusted to a condition 330' of greater curvature or to a position of lesser curvature (not shown). Diaphragm 330 may have a structure similar to the structure of the beam-type transducer element discussed above, and desirably includes a continuous layer of a piezoelectric film with electrodes 336 and 338 disposed on opposite sides of the piezoelectric film. However, the electrodes desirably are disposed in a two-dimensional array on the surface of the diaphragm. In a variant of this arrangement, a control element may be connected to the diaphragm at its center for bending the diaphragm to a more curved or less curved condition. Curvature of such a diaphragm may be detected by impedance monitoring or other techniques as discussed above.

Apparatus according to a further embodiment of the invention (FIGS. 10 and 11) includes a set of supports 402. Each support has a central end 404 and a peripheral end 406. The central ends of these supports are pivotally connected to a common member 408, which in turn is connected to the control element or cable 450. A set of struts 410 is also provided. Each strut is pivotally connected to one of the supports 402 between its central end 404 and peripheral end 406. Each strut is also pivotally connected to a control member 412. Control member 412 is mounted to the distal end 424 of the probe body 420. Individual transducer elements 430 are mounted to the supports 402 adjacent the peripheral ends thereof. The transducer may be moved between the collapsed or closed configuration illustrated in FIG. 10 to the expanded condition illustrated in solid lines in FIG. 11, and to the further expanded, over-center condition partially illustrated in broken lines in FIG. 11 by moving the control cable or control element 450 relative to the probe body 420 so as to move the common member 408 relative to control member 412. In the collapsed or closed configuration (FIG. 10), supports 402 lie close to the axis 462 of the probe body. In the expanded condition, the supports project outwardly away from axis 462. In the expanded, over center position depicted in broken lines in FIG. 11, the various individual transducers 430' will tend to focus their ultrasonic energy on a common focal location. The position of such focal location can be adjusted by moving the common member 408 relative to control member 412 so as to pivot the supports 402.

Alternatively or additionally, transducers 432 may be provided on the opposite sides of the support. Transducers 432 are directed towards a common focus when the supports are in the condition illustrated in solid lines in FIG. 11. In still further variants, the connection of the control member 412 and of common member 408 may be reversed. Thus, control member 412 may be connected to cable or control element 450 whereas common member 408 may be mounted to the probe body. Also, the initial positions of the elements may be reversed so that in the collapsed condition, the supports 402 and struts 410 extend rearwardly along the probe body rather than forwardly from the distal tip of the probe body. Of course, the number of supports and struts may be varied. Also, the measures discussed above for monitoring the curvature of a continuous curved transducer may be used in the case of a transducer having discrete transducer elements and separate supports. Thus, position sensors may be provided on supports 402. Alternatively, the position of the control element 450 relative to the probe body 420 may be monitored.

Figure 10:
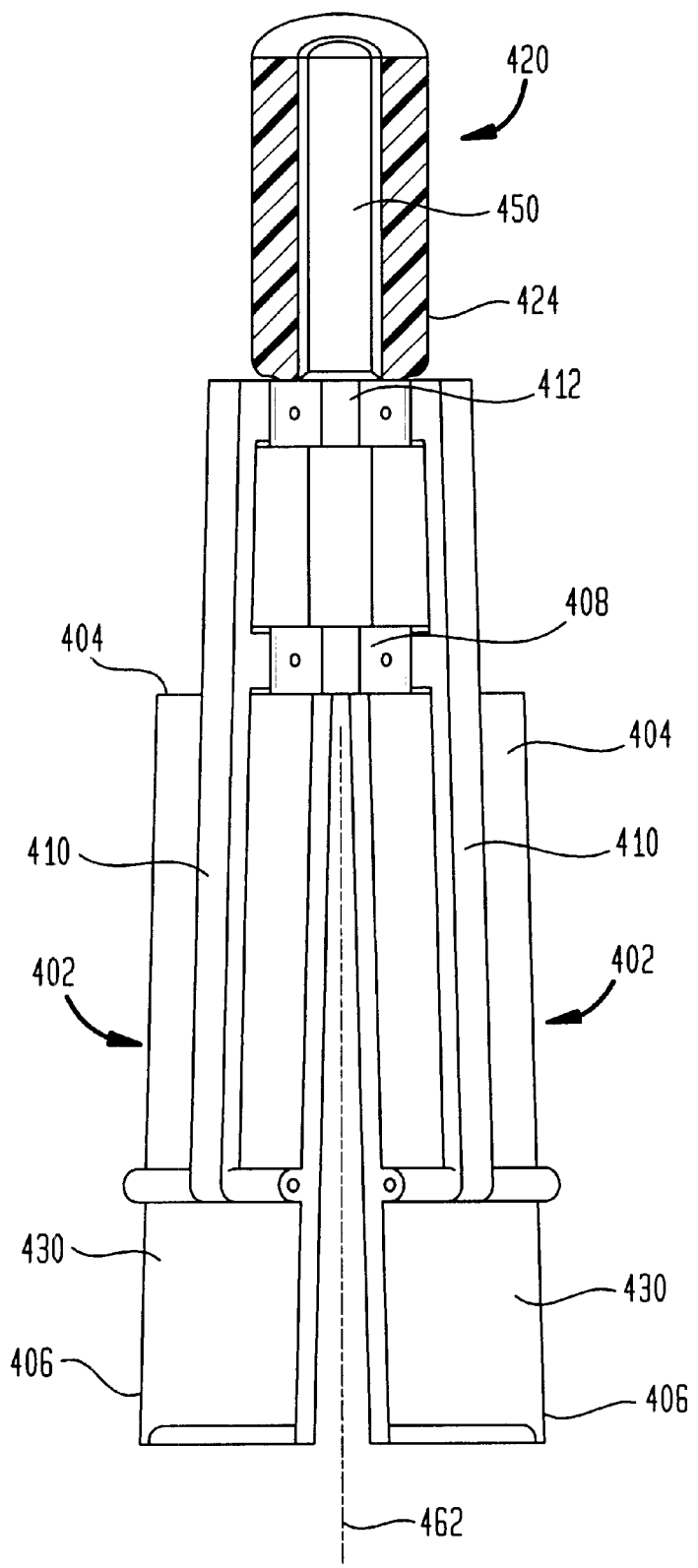
FIG. 10 is a fragmentary, perspective view depicting portions of a probe in accordance with another embodiment of the invention.
Figure 11:
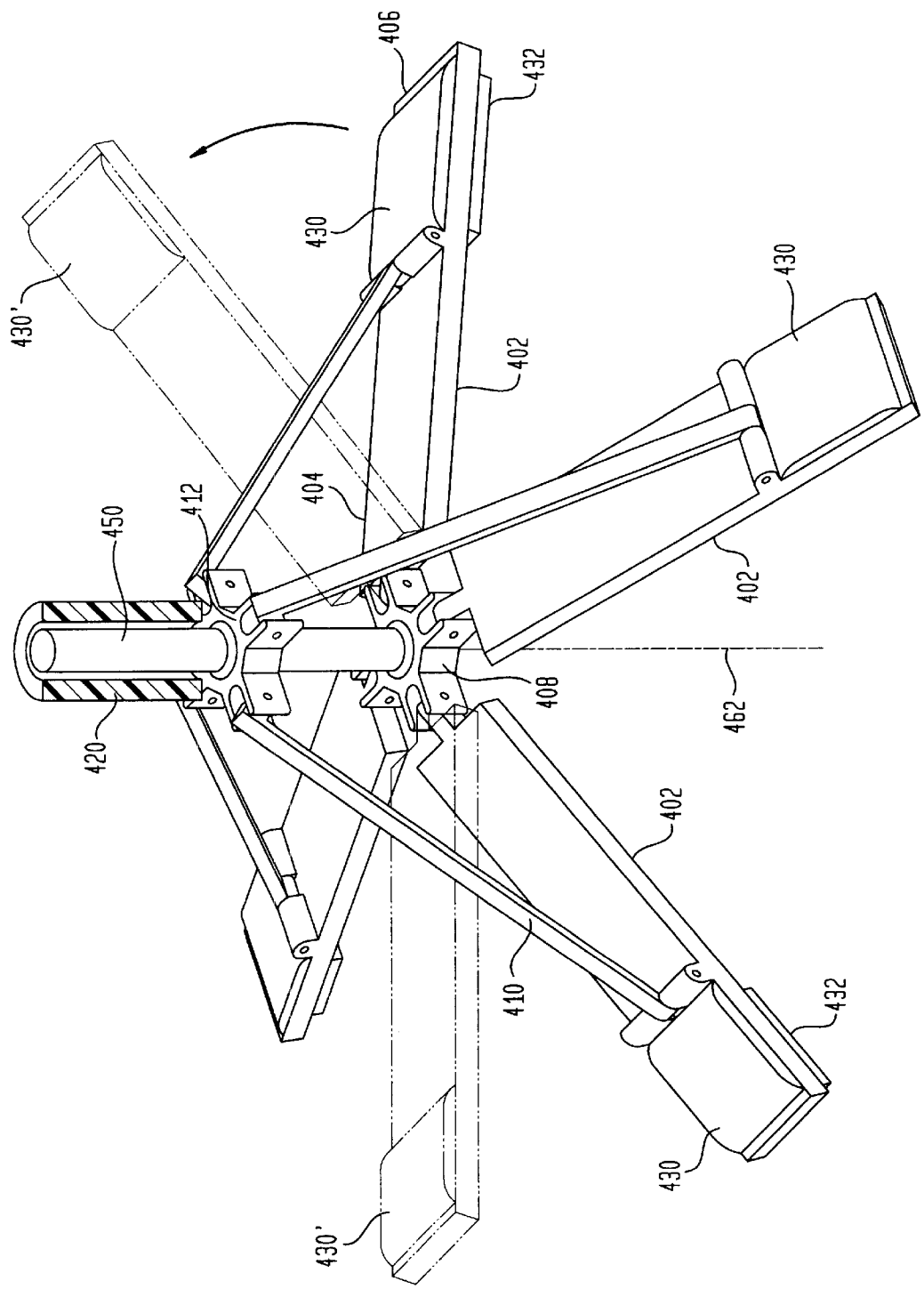
FIG. 11 is a view similar to FIG. 10 but depicting the a probe of FIG. 10 in a different condition during operation.

A transducer assembly as shown in FIGS. 10 and 11 can be used by advancing it in the closed or collapsed condition into a natural body cavity as, for example, the urinary bladder and then expanding the transducer assembly and bringing the transducer elements to the appropriate locations to focus energy on a lesion as, for example, a lesion within the prostate gland. After therapy, the assembly desirably is returned to the closed or collapsed configuration and extracted from the patient.

Probes as discussed above may be provided with balloons or other flexible shields (not shown) covering the ultrasonic transducer. In use, such a shield is filled with a liquid such as water or saline solution, so that the shield bears against the surrounding tissues. Ultrasonic energy from the transducer is transmitted through the liquid and the shield to the patient's body. Liquid may be circulated through the probe body, into and out of the shield, to cool the transducer.

Figure 12:
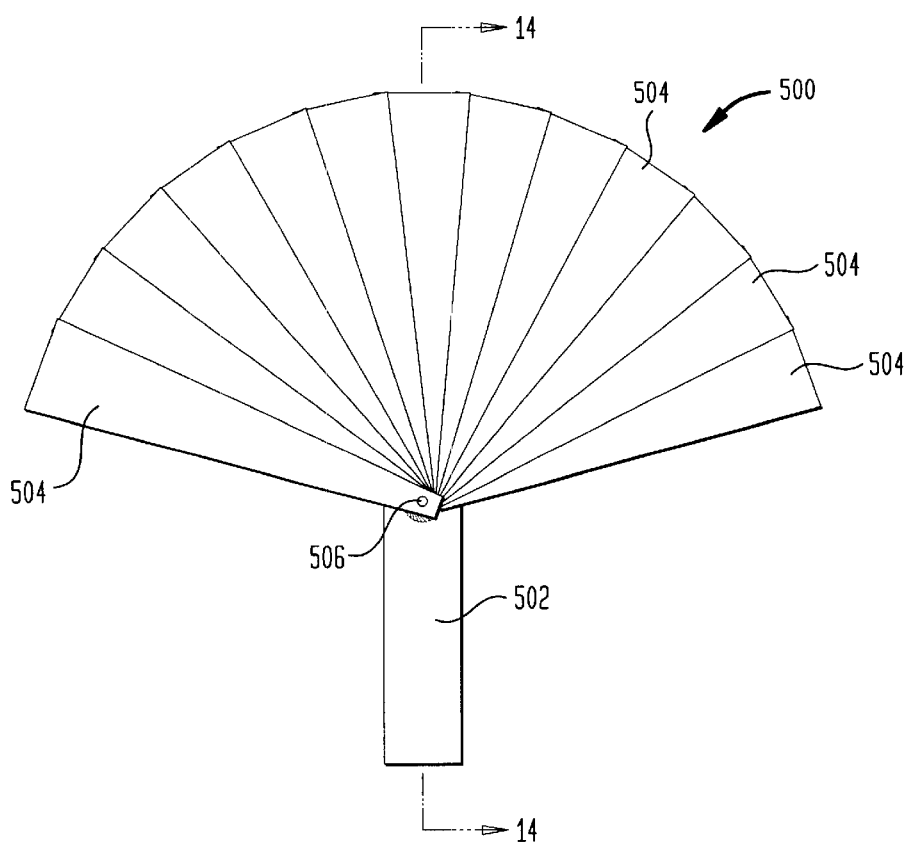
FIG. 12 is a fragmentary diagrammatic elevational view depicting portions of a probe in accordance with another embodiment of the invention in one condition during operation.
Figure 13:
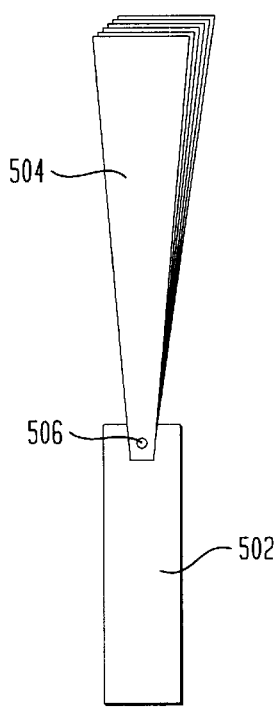
FIG. 13 is a view similar to FIG. 10 but depicting the probe of FIG. 12 in a different condition during operation.
Figure 14:
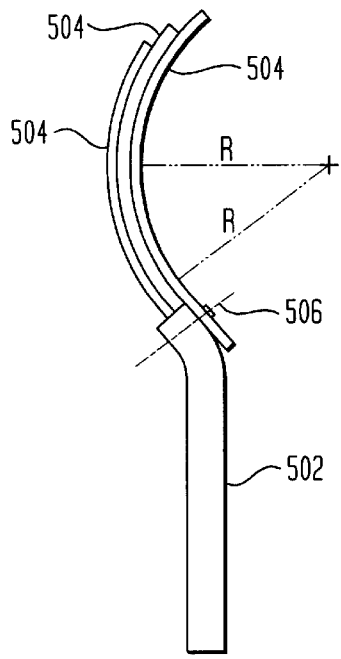
FIG. 14 is a diagrammatic sectional view taken along line 14—14 in FIG. 12.

A probe according to a further embodiment of the invention (FIGS. 12–14) includes a spatially-distributed collapsible transducer 500 mounted to the distal end of an elongated probe 502. Transducer 500 incorporates a plurality of leaves 504. As seen in plan view (FIGS. 12 and 13) each leaf is generally wedge-shaped, having a narrow end and a broad end. As seen in section (FIG. 14) each leaf is curved. Each leaf has one or more transducer elements thereon. For example, each leaf may include a continuous piezoelectric layer with one or more electrodes as discussed above, or with a set of discrete transducers. The narrow ends of the leaves are pivotally connected to one another and to the probe body 502 for movement about a common pivot axis 506 transverse to the direction of elongation of the probe. The leaves are movable between the collapsed condition of FIG. 13 the expanded condition of FIG. 12. In the expanded condition, the leaves wholly or partially overlie one another, whereas in the expanded condition at least a portion of each leaf is exposed and is not covered by another leaf. As the transducer expands or collapses, the leaves slide over one another. The collapsing and expanding action is similar to the action of a traditional Japanese fan. The collapsing and expanding action can be controlled by control cables or other elements (not shown) extending through the probe. Alternatively or additionally, the collapsing or expanding action can be driven by spring mechanisms, electrical, hydraulic or pneumatic mechanisms, or even by a small electric motor disposed adjacent the distal end of the probe. Thermally-responsive elements such as bimetallic or shape-memory metals can be employed.

In the collapsed condition, the distributed transducer is small; all of the leaves lie close to the axis of probe body 502. Therefore, the transducer can be advanced readily into a body cavity. For example, the probe may be inserted vaginally, rectally or orally and expanded inside the body of the patient. Desirably, the radius of curvature of each leaf is selected so that sonic energy emitted from all of the leaves when the leaves are in the expanded condition is focused to a common point, line or region. The leaves may be rigid or flexible. If the leaves are flexible, control elements (not shown) similar to those discussed above may be provided for deforming the individual leaves or deforming the leaves together, and devices for monitoring the deformation of the leaves may be provided as discussed above for monitoring individual deformable elements.

Figure 15:
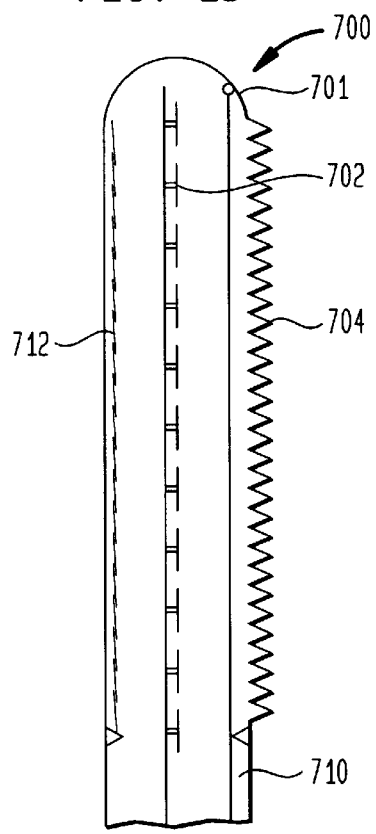
FIG. 15 is a fragmentary diagrammatic sectional view depicting a probe in accordance with yet another embodiment of the invention.
Figure 16:
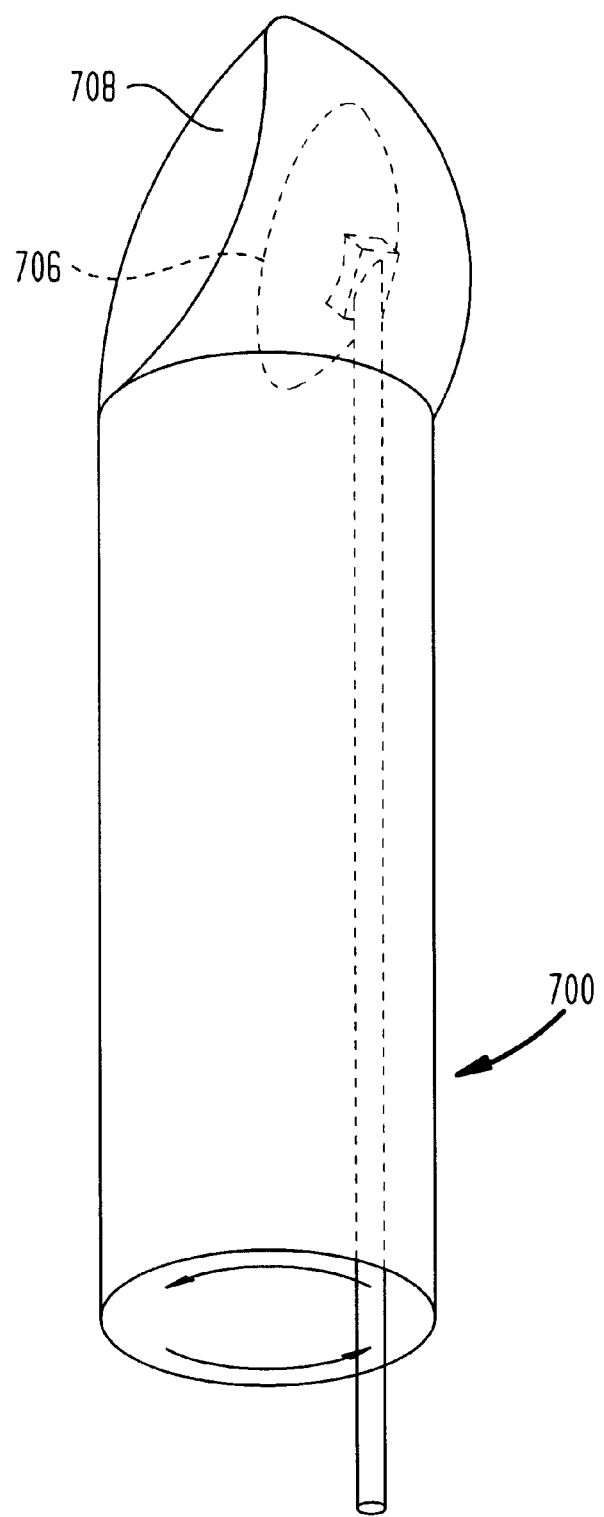
FIG. 16 is a fragmentary diagrammatic view depicting a probe in accordance with yet another embodiment of the invention.

The embodiment depicted in FIG. 15 illustrates one way of implementing a bendable catheter 700 or other probe with a transducer 702 distributed lengthwise along its distal end, as discussed above with reference to FIG. 8. The interior of the probe distal end desirably is filled with a liquid, gel or other energy-transmissive medium so that sound can be transmitted from the transducers 702 through the accordion-pleated wall 704 of the probe. A cable 710 is provided with one end attached to the distal end of the probe so that the probe 700 can be bent. The side opposite the accordion-pleated wall 704 of the probe may have expandable sides 712 to accommodate the bending of the probe. As shown in FIG. 16, movable transducer in the form of a rigid emitting dish 706 of suitable diameter is housed inside a liquid or gel filled probe body having a balloon-like transmission window 708. The emitting dish is movably mounted to the probe body, so that the location of the focal spot can be moved by moving the dish.

Figure 17:
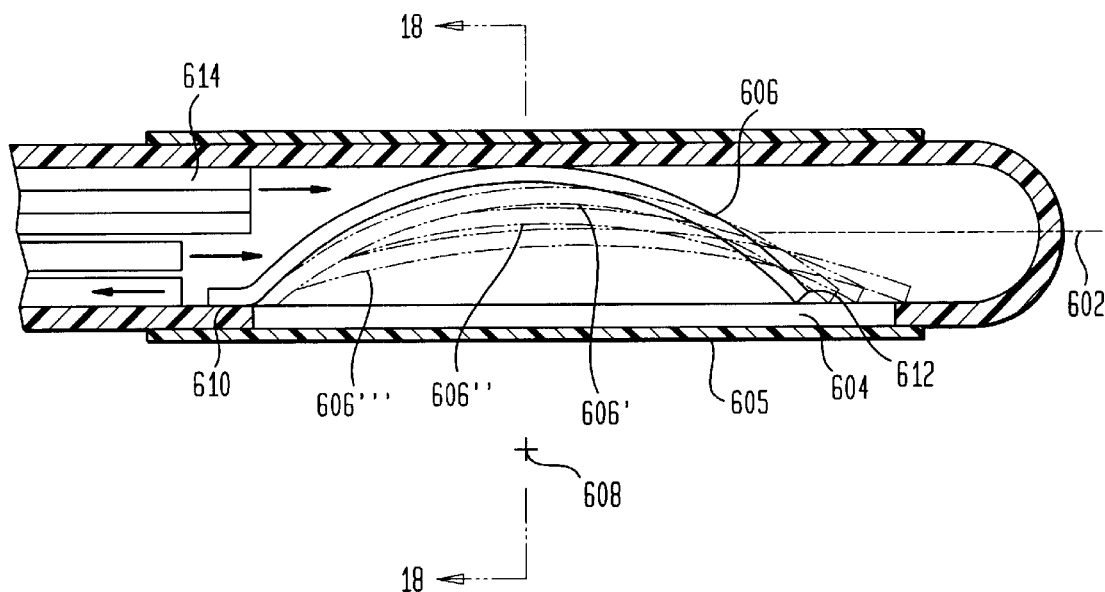
FIG. 17 is a fragmentary diagrammatic sectional view depicting a probe in accordance with yet another embodiment of the invention.
Figure 18:
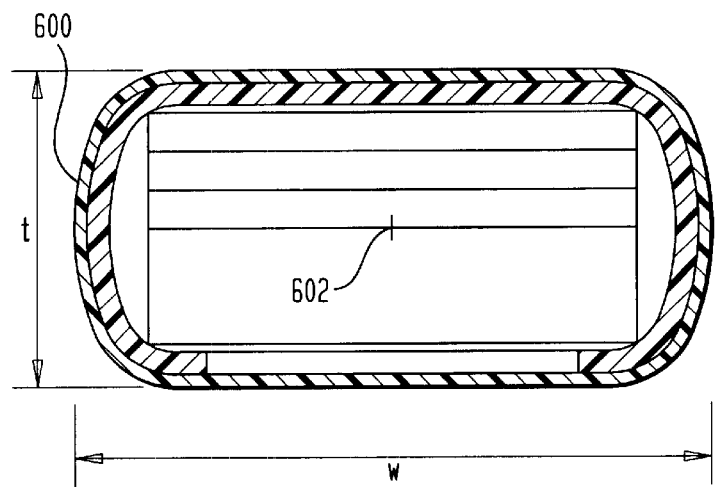
FIG. 18 is a sectional view along line 18—18 in FIG. 17.

The probe depicted in FIGS. 17 and 18 has a hollow body 600 having a noncircular cross-sectional shape adjacent its distal end, so that the probe body defines dimension w in a widthwise direction larger than its dimension t in a thickness direction, both such directions being transverse to the axis of elongation 602 of the probe. The distal end of the probe body desirably is formed from a rigid polymer such as polycarbonate, whereas the remainder of the probe may be flexible or rigid. The cross-sectional shape may be uniform throughout the length of the probe, or may gradually merge into a circular or other shape adjacent the proximal end of the probe body (not shown). The probe body has a window 604 extending lengthwise along the probe and extending in the widthwise direction of the probe. The window is covered by a thin energy-transmissive membrane such as a film or shrink band formed from a polymer such as polyimide or glycol-modified polyethelyene terephtalate ("PETG"). A spatially-distributed transducer 606 is mounted in the probe body. Transducer 606 has an emitting surface facing towards the window, generally in the thickness direction t. Transducer 606 also extends in the widthwise direction and lengthwise directions of the probe body. The projected area of transducer 606 is greater than the projected area of a transducer which could fit within a probe body of circular cross section having the same cross-sectional area. All else being equal, this provides greater sonic energy emission in a probe which can be threaded into a given bodily cavity or orifice.

Transducer 606 is deformable. The transducer may include a unitary piezoelectric layer or a set of plural piezoelectric devices mounted to a deformable element. The transducer may include a beam-like element as discussed above, curved about an axis of curvature 608 which extends in the widthwise direction of the probe body. One end of the beam, desirably the proximal end 610, is fixed to the probe body, whereas the opposite end 612 is free to slide within the probe body. One or more slide elements 614 are disposed within the probe body. The slide elements are connected to control devices (not shown) allowing the user to selectively slide one or more of the slide elements from the disengaged positions illustrated in FIG. 17 to engaged positions in which the slide elements are disposed between transducer 606 and the wall of the probe body. The control devices may include portions of the slide elements 614, or cables connected thereto, extending to the proximal end of the probe body so that the user can selectively manipulate the slide elements. Other devices such as hydraulic, pneumatic or electromechanical actuators can be used. In a rest condition, with all of the slide elements in their disengaged positions, transducer 606 rests against the rear wall of the probe body opposite from window 604. In this condition, transducer 606 has a minimum radius of curvature. The user can change the curvature of the transducer by advancing one or more of the slide elements to engaged positions as indicated at 614' in FIG. 17. As the slide elements are engaged, the transducer is deformed to less-curved positions 606', 606", etc. With each combination of engaged and disengaged slide elements, the transducer has a known curvature. Therefore, there is no need for measurement devices to monitor the degree of curvature of the transducer.

The probe further includes cooling fluid passages 616 for conducting a coolant such as water or other energy-transmissive liquid into and out of the probe distal end. These passages may be formed integrally with the probe body, or may be formed integrally with one or more of the slide elements.

In a variant of the probe shown in FIGS. 17 and 18, the transducer may be generally dome shaped, so that the transducer is curved about a first axis transverse to the axis of elongation of the probe body and along a second axis parallel to the axis of elongation of the probe body. One spot on the transducer is secured to the probe body. Here again, moving the slide elements into or out of engaged positions serves to flatten the dome to some degree or to allow the dome to return to a more curved condition. Also, although the term "slide element" is used in the above discussion for ease of reference, the slide elements can be brought into and out of their respective engaged positions by rotary or other movement rather than sliding motion.

In the embodiments discussed above, the ultrasonic transducers include piezoelectric elements. However, the invention can also be applied with other types of ultrasonic transducers as, for example, magnetostrictive elements.

As these and other variations and combinations of the features discussed above can be utilized, the foregoing description of the preferred embodiment should be taken by way of illustration rather than by way of limitation of the invention.

The following claims further illustrate certain aspects of the invention:

1. A probe for applying sonic energy within the body of a subject comprising:
   (a) a probe body having a proximal end and a distal end adapted for insertion into the body of the subject;
   (b) a spatially-distributed sonic transducer disposed adjacent said distal end of said probe body, said sonic transducer including a continuous transducer sheet, said sonic transducer being operative to apply therapeutic ultrasonic energy so as to heat tissues within the body of a subject to a temperature sufficient to create a therapeutic effect; and
   (c) means for moving one portion of said transducer relative to another portion of said distributed transducer while said distal end of said probe is disposed within the body of the subject.

2. A probe as claimed in claim 1 wherein said distributed transducer includes a deformable element mounted to said probe body adjacent the distal end thereof, said means for moving including means for controlling deformation of said deformable element.

3. A probe as claimed in claim 2 wherein said deformable element is integral with said transducer sheet.

4. A probe as claimed in claim 2 wherein said distributed transducer includes a plurality of separate transducer elements mounted to said deformable element at spaced-apart locations thereon.

5. A probe as claimed in claim 2 wherein said deformable element includes an elongated beam having a fixed end mounted to said probe body and a free end, said means for controlling deformation including a control element movably mounted to said probe body, said control element having a distal end connected to said free end of said beam and having a proximal end extending to the proximal end of said probe.

6. A probe as claimed in claim 5 wherein said control element includes a flexible cable.

7. A probe as claimed in claim 6 wherein said probe body includes an elongated tubular element, and said flexible cable extends through said tubular element.

8. A probe as claimed in claim 2 wherein said deformable element includes a central region and a peripheral region surrounding said central region, said means for controlling deformation including means for moving said peripheral and central regions relative to one another.

9. A probe as claimed in claim 8 wherein said means for controlling deformation includes a control element movably mounted to said probe body, said control element connected to one portion of said deformable element, another portion of said deformable element being connected to said probe body so that movement of said control element relative to said probe body will deform said deformable element.

10. A probe as claimed in claim 1 wherein said transducer sheet includes a piezoelectric layer, and wherein said piezoelectric layer has electrical impedance varying with strain.

11. A probe as claimed in claim 10 wherein said transducer includes strain-sensing electrodes in contact with said piezoelectric layer at spaced-apart locations thereon, whereby electrical impedance between said strain-sensing electrodes is related to deformation of said deformable element.

12. A probe for applying sonic energy within the body of a subject comprising:
   (a) a probe body having a proximal end and a distal end adapted for insertion into the body of the subject, said distal end of probe body being deformable;
   (b) a spatially-distributed sonic transducer mounted to said distal end of said probe body and mounted to said probe body so that deformation of said distal end of said probe body will move one portion of said sonic transducer relative to another portion of said sonic transducer; and
   (c) means for deforming said distal end of said probe body while said distal end of said probe is disposed within the body of the subject.

13. A probe as claimed in claim 12 wherein said probe body is elongated, said distributed transducer extends in a lengthwise direction of said probe body adjacent the distal end of the probe body, and said means for deforming the distal end of the probe body includes means for bending the distal end of the probe body transverse to its lengthwise direction.

14. A probe as claimed in claim 12 wherein said sonic transducer is operative to apply therapeutic ultrasonic energy so as to heat tissues within the body of a subject to a temperature sufficient to create a therapeutic effect.

15. A probe as claimed in claim 12 or claim 11 or claim 13 wherein deformation of said distal end of said probe body to a curved shape deforms said distributed sonic transducer so as to focus ultrasonic energy from said sonic transducer within a focal region.

16. A probe for applying sonic energy within the body of a subject comprising:
   (a) a probe body having a proximal end and a distal end adapted for insertion into the body of the subject;
   (b) a spatially-distributed sonic transducer disposed adjacent said distal end of said probe body;
   (c) a plurality of supports movable relative to the probe body, said distributed transducer including a plurality of transducer elements mounted to said supports; and
   (d) means for moving one or more of said supports relative to said probe body so as to move one of said transducer elements relative to another one of said transducer elements.

17. A probe as claimed in claim 16 wherein said plurality of supports includes a plurality of elongated supports having central ends pivotally connected to a common member and having peripheral ends remote from said central ends, said transducer elements being mounted to said elongated supports adjacent said peripheral ends, said means for moving one or more of said supports including means for pivoting said supports relative to said common member between a collapsed condition in which said peripheral ends are close to a central axis and an expanded condition in which said peripheral ends are remote from said central axis.

18. A probe as claimed in claim 17 wherein said means for pivoting includes a control member and a plurality of struts, each said strut having a first end pivotally connected to said control member and a second end connected to one of said elongated supports remote from the central end thereof, said means for pivoting said supports including means for moving said control member towards and away from said common member.

19. A probe as claimed in claim 18 wherein said probe body includes an elongated tubular element, said means for moving said control member including a flexible cable extending through said tubular element, one of said common member and said control member being connected to said tubular element, the other one of said common member and said control member being connected to said flexible cable.

\* \* \* \* \*

UNITED STATES PATENT AND TRADEMARK OFFICE
CERTIFICATE OF CORRECTION

PATENT NO. : 6,461,314 B1
DATED : October 8, 2002
INVENTOR(S) : Bharat B. Pant, David E. Acker and Edward Paul Harhen It is certified that error appears in the above-identified patent and that said Letters Patent is hereby corrected as shown below:

<u>Column 14,</u>
Line 19, "claim 11" should read -- claim 14 --.

Signed and Sealed this

Twentieth Day of May, 2003

JAMES E. ROGAN
*Director of the United States Patent and Trademark Office*